US010124310B2

(12) United States Patent
Thuo et al.

(10) Patent No.: US 10,124,310 B2
(45) Date of Patent: Nov. 13, 2018

(54) MICRO- AND NANO-PARTICLES WITH VARIABLE SURFACE MORPHOLOGIES AND METHODS OF MAKING SAME

(71) Applicant: MASSACHUSETTS, UNIVERSITY OF, Boston, MA (US)

(72) Inventors: Martin Thuo, Ames, IA (US); Ian Tevis, Brighton, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 15/521,518

(22) PCT Filed: Oct. 27, 2015

(86) PCT No.: PCT/US2015/057586
§ 371 (c)(1),
(2) Date: Apr. 24, 2017

(87) PCT Pub. No.: WO2016/069604
PCT Pub. Date: May 6, 2016

(65) Prior Publication Data
US 2017/0326523 A1 Nov. 16, 2017

Related U.S. Application Data

(60) Provisional application No. 62/069,063, filed on Oct. 27, 2014.

(51) Int. Cl.
B82Y 30/00 (2011.01)
B01J 13/22 (2006.01)
(Continued)

(52) U.S. Cl.
CPC ............... B01J 13/22 (2013.01); A61K 9/143 (2013.01); A61K 9/145 (2013.01); B01J 23/08 (2013.01);
(Continued)

(58) Field of Classification Search
CPC .......... B82Y 30/00; B82Y 40/00; B01J 13/22
See application file for complete search history.

(56) References Cited

U.S. PATENT DOCUMENTS 7,455,714 B2 11/2008 Sato
2007/0141333 A1 6/2007 Shastri et al.
(Continued)

OTHER PUBLICATIONS

Tevis et al, Syntesis of Liquid Core-Shell Particles and Solid Patchy Multicomponent Particles by Shearing Liquids Into Complex Particles (SLICE), Langmuir, 2014, 30 (47), 14308-14313.*
(Continued)

Primary Examiner — Carlos A Azpuru
(74) Attorney, Agent, or Firm — Lando & Anastasi, LLP

(57) ABSTRACT

A method of making a multilayer metal particle having an irregular surface architecture includes introducing a molten eutectic metal alloy into a solution to produce a eutectic-solvent mixture, shearing the eutectic-solvent mixture for a sufficient period of time to induce surface tension driven phase segregation in the molten eutectic metal alloy to produce an irregular surface architecture on the eutectic metal alloy, allowing the molten eutectic metal alloy to precipitate to produce a plurality of particles, allowing the plurality of particles to oxidize in the presence of an oxidizer, and functionalizing the particles with an organic species to form an organic layer to produce a multilayer metal particle having an irregular surface architecture.

25 Claims, 7 Drawing Sheets

(51) Int. Cl.
| | | |
|---|---|---|
| *B22F 1/00* | (2006.01) | |
| *B22F 1/02* | (2006.01) | |
| *B22F 9/08* | (2006.01) | |
| *A61K 9/14* | (2006.01) | |
| *B01J 23/08* | (2006.01) | |
| *B01J 23/14* | (2006.01) | |
| *B01J 23/18* | (2006.01) | |
| *B01J 31/02* | (2006.01) | |
| *B01J 35/00* | (2006.01) | |
| *B01J 35/02* | (2006.01) | |
| *B01J 37/00* | (2006.01) | |
| *B01J 37/02* | (2006.01) | |
| *B22F 9/06* | (2006.01) | |
| *B22F 9/14* | (2006.01) | |
| *B82Y 40/00* | (2011.01) | |

(52) U.S. Cl.
CPC ............... *B01J 23/14* (2013.01); *B01J 23/18* (2013.01); *B01J 31/0212* (2013.01); *B01J 35/0006* (2013.01); *B01J 35/026* (2013.01); *B01J 37/0072* (2013.01); *B01J 37/0219* (2013.01); *B01J 37/0221* (2013.01); *B01J 37/0244* (2013.01); *B22F 1/0044* (2013.01); *B22F 1/0062* (2013.01); *B22F 1/02* (2013.01); *B22F 9/06* (2013.01); *B22F 9/08* (2013.01); *B22F 9/14* (2013.01); *B22F 2998/10* (2013.01); *B82Y 30/00* (2013.01); *B82Y 40/00* (2013.01)

(56) References Cited

U.S. PATENT DOCUMENTS

| | | |
|---|---|---|
| 2011/0212386 A1 | 9/2011 | Roller et al. |
| 2011/0288215 A1 | 11/2011 | Shultz et al. |
| 2013/0244037 A1 | 9/2013 | Hohman et al. |

OTHER PUBLICATIONS

Raabe, D et al., "Synthesis of hollow metallic particles via ultrasonic treatment of a metal emulsion." Scripta Materialia. vol. 62, No. 9. (2010) p. 690-692; Abstract, p. 690, col. 2, paragraph 2.

Lowengrub, J et al., "Surface phase separation and flow in a simple model of multicomponent drops and vesicles." Fluid Dyn. Mater. Proc 3.1 (2007) p. 1-19; p. 2, col. 2, paragraph 2; p. 3, col. 1, paragraph 1; p. 13, col. 2, paragraph 3.

Eaker, CB. "Surface Characterization and Manipulation of Eutectic Gallium Indium in Aqueous Media" (2012) p. 1-70; Retrieved online: <URL:https://scholar.google.com/scholar?hl=en&q=Surface+Characterization+and+Manipulation+of+Eutectic+Gallium+Indium+in+Aqueous+Media.&btnG=8,as_sdt=1%2C3&as_sdtp+>; p. 18-19.

* cited by examiner

MICRO- AND NANO-PARTICLES WITH VARIABLE SURFACE MORPHOLOGIES AND METHODS OF MAKING SAME

CROSS-REFERENCE TO RELATED APPLICATIONS

This application is a U.S. national phase application and claims the benefit of priority under 35 U.S.C. § 371 of International (PCT) Patent Application Serial No. PCT/US2015/057586, titled "MICRO- AND NANO-PARTICLES WITH VARIABLE SURFACE MORPHOLOGIES AND METHODS OF MAKING SAME," filed Oct. 27, 2015, which in turn claims priority under 35 U.S.C. § 119(e) to U.S. Provisional Patent Application Ser. No. 62/069,063, titled "MICRO- AND NANO-PARTICLES WITH VARIABLE SURFACE MORPHOLOGIES AND METHODS OF MAKING SAME," filed Oct. 27, 2014, which is hereby incorporated herein by reference in its entirety for all purposes.

TECHNICAL FIELD

The technical field relates generally to micro- and nano-sized particles derived from low-temperature melting point metals and metal alloys.

SUMMARY

Aspects and embodiments are generally directed to particles having variable surface morphologies and methods of making the same.

In accordance with one or more aspects, a method of making a multilayer metal particle having an irregular surface architecture may comprise introducing a molten eutectic metal alloy into a solution to produce a eutectic-solvent mixture, shearing the eutectic-solvent mixture for a sufficient period of time to induce surface tension driven phase segregation in the molten eutectic metal alloy to produce an irregular surface architecture on the eutectic metal alloy, allowing the molten eutectic metal alloy to precipitate to produce a plurality of particles, allowing the plurality of particles to oxidize in the presence of an oxidizer, and functionalizing the particles with an organic species to form an organic layer to produce a multilayer metal particle having an irregular surface architecture.

In some non-limiting aspects, the period of time for shearing may be in the range of about 5 minutes to about 30 minutes. The particles may be functionalized with a carboxylate species, such as a carboxylate species comprising acetate. The solution may comprise acetic acid. The solution may comprise acetic acid and a solvent having a boiling point below 250° C. to produce a 5% acetic acid solution. The solvent may comprise one of water or diethylene glycol. The molten eutectic metal alloy may be a three-component alloy with a melting point below 200° C. The molten eutectic metal alloy may comprise Field's metal having 32.5% bismuth, 51% indium, and 16.5% tin by weight.

In other non-limiting aspects, the method may further comprise drying the particles to induce the formation of self-assembled aggregated particles. The method may further comprise heating the eutectic-solvent mixture before shearing. The eutectic-solvent mixture may be heated to a temperature in a range of from about 95° C. to about 160° C. The method may further comprise cooling the mixture to room temperature during the shearing step. The method may comprise a step of milling the multilayer particle into a desired shape. Milling may generally comprise subjecting the multilayer particle to a focused ion beam.

In accordance with one or more aspects, a multilayer nano- or micro-particle may comprise at least three metals and have an irregular surface architecture.

In some non-limiting aspects, the multilayer particle may comprise an interior core, a surrounding oxide layer, and a surface organic layer. The irregular surface architecture may comprise at least one of the following: a lamellar texture, a smooth woven texture, a rough solid texture, a rough porous surface, and a porous texture. The multilayer particle may comprise bismuth, indium, and tin. The multilayer particle may comprise Field's metal. The oxide layer may comprise at least one of indium oxide and tin oxide. The surface organic layer may comprise acetate or a carboxylate species. The carboxylate species may comprise acetate. The oxide layer may have a thickness of at least about 0.7 nm.

In accordance with one or more aspects, a pharmaceutical agent or a catalyst may comprise the multilayer particles as described herein.

Still other aspects, embodiments, and advantages of these example aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Embodiments disclosed herein may be combined with other embodiments, and references to "an embodiment," "an example," "some embodiments," "some examples," "an alternate embodiment," "various embodiments," "one embodiment," "at least one embodiment," "this and other embodiments" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

In accordance with one or more embodiments, multilayer metal particles and methods of producing them are disclosed. The particles may have a variable surface morphology with varying degrees of surface roughness and a varying composition at different portions of the particle surface, resulting in a patchy multi-component particle.

These particles may be prepared via a low-cost method which does not rely on sonication and/or polymers to scission metal into a desired size. Centrifugal shearing forces in the presence of surface acting molecules and temperature control may yield the patchy, multicomponent metal particles. The particles may be made by phase separation and/or by selective etching of a metal alloy. An environmentally benign technique may be used which does not require advanced equipment. Synthesis may generally involve placing a molten alloy in solution, shearing the molten alloy, promoting surface reactions to give an oxide and/or an organic layer, and inducing phase segregation of an alloy leading to accumulation of one or more metals at different portions of the particle. The particles may also be selectively etched to vary their characteristics. The fabricated particles may find wide use in a variety of applications.

In accordance with one or more embodiments, fabrication of patchy multicomponent, metal micro- and nano-particles may use shearing force, surface tension, centrifugal, and/or centripetal forces generated by stirring a metal (liquid at ambient or molten by heating) in the presence of a Newtonian liquid. The stirring can be done in the presence of a reagent that may modify the surface of the metal and/or may selectively etch one metal component over the other. Aqueous solutions and common benign reagents may be used to fabricate these particles with tunable sizes. The processes, shearing, and low power (reaction time in the minutes timescale) make the disclosed techniques a very environmentally benign way to make complex nanoparticles. The methods disclosed herein may provide one or more advantages over other currently available methods. For example, the methods disclosed herein may be used to create micro- and nano-sized particles that are tunable, green (eco-friendly), and inexpensive.

Figure 1:
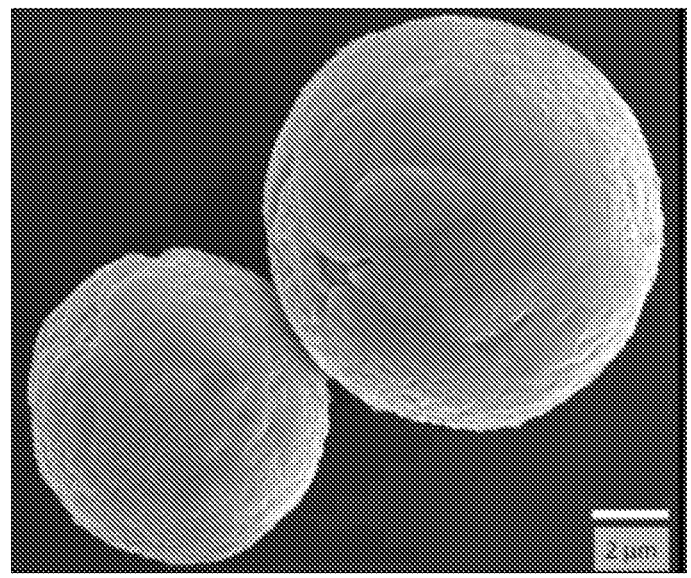
FIG. 1 is a scanning electron microscope (SEM) image of a pair of variable-surface particles in accordance with one or more aspects of the invention.
Figure 2:
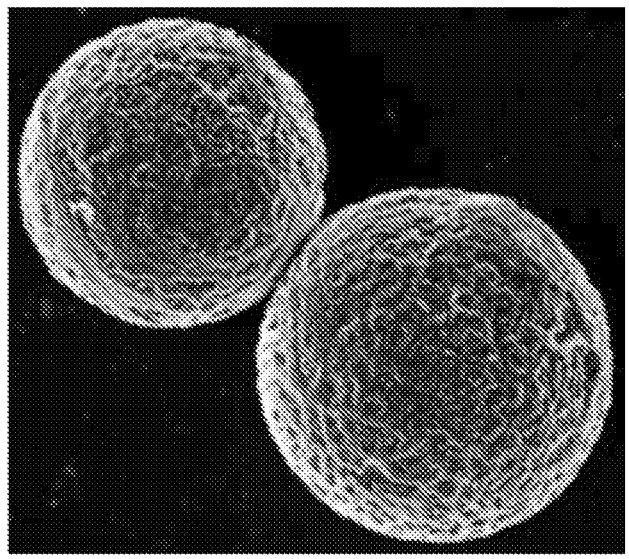
FIG. 2 is an SEM image of a pair of variable-surface particles in accordance with one or more aspects of the invention.
Figure 3:
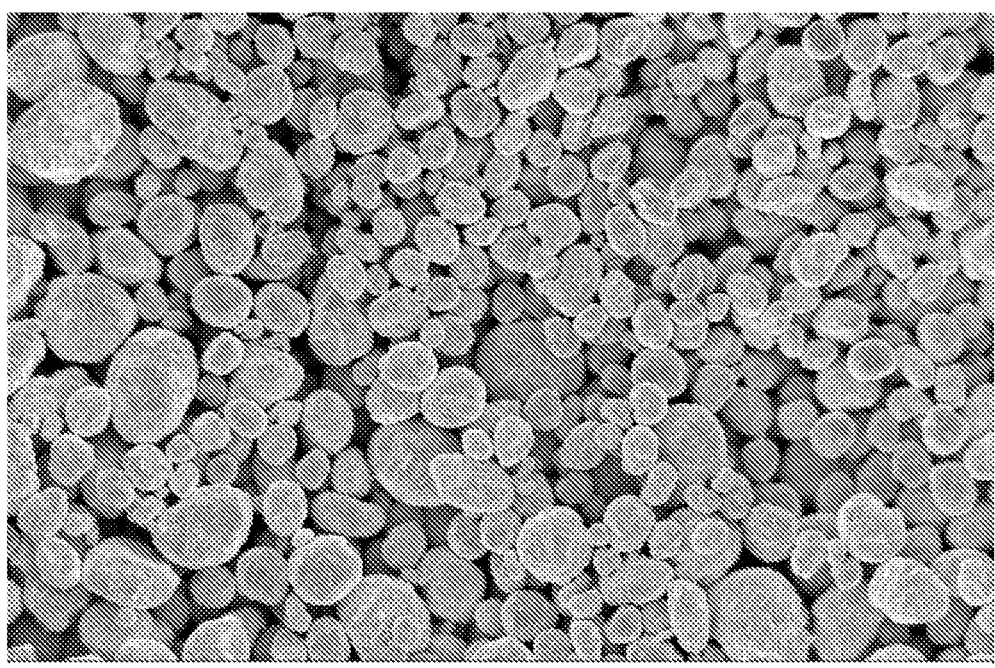
FIG. 3 is an SEM image of variable-surface particles of various sizes in accordance with one or more aspects of the invention.

The multi-layer particles generated can be produced in many sizes (meso-, micro-, or nanoscale). The patchy regions can be 100% a single metal or can be enriched in one metal over the alloy composition. The surface of these patchy particles can also be varied depending on how the particles are prepared. Multi-layered particles synthesized by the disclosed methods can be further developed to create complex surface architectures through chemical grafting of the outer layer, self-assembly, or selective reaction. The particles can be made into different shapes and sizes as shown in FIGS. 1-3. The particles may have different degrees of surface roughness in comparison to conventional particles which may be dictated by the phase segregation process and the cooling rate.

In various embodiments, shearing force, selective etching, and other factors can be strategically adjusted to produce particles of different qualities, sizes and shapes. Nano- and micro-wires, and multi-layered nanosheets may also be fabricated via the disclosed techniques. Further discussion of particles that may be formed through the application of shearing forces may be found in International (PCT) Patent Application Serial No. PCT/US2014/069802 (Publication No. WO2015/089309), titled "CORE-SHELL MULTI-LAYER PARTICLES," which is incorporated by reference herein in its entirety and for all purposes.

In some embodiments, the particles may be used in pharmaceutical, imaging, optical, or consumer product applications. In terms of imaging, these particles can be used in plasmonics. The difference in density among the multilayers can be tuned to manipulate surface plasmons and as such can act as surface waveguides (especially in the nanowire configuration or with a second layer of metal on them). These particles can also be used as contrast agents in medical imaging. In terms of diagnostics, the organic layer can be used as an anchor for biomolecules. The attached biomolecules can be used to probe for disease in vivo or for signal amplification in diagnostic tests like ELISA. The particles can be dispersed into liquids and used to create mirror coatings on solid objects. These metal coatings could be used to block RF and/or aid in heat transfer. The particles may be used to produce a nanosolder material. By coating the particles in a charged organic layer, the particles can be manipulated using an electric field and can then be printed as a metallic ink. The particles can be used as thermal sensors where thermal expansion and melting of the particles can result in an electrical trigger. The particles may be used in catalysis in which a particle can perform different reactions. The particles may also be used in optics making use of them exhibiting different reflectivity. The particles may be used in the synthesis of various composite materials for a wide range of industries.

Aspects of this disclosure relate to scalable systems and methods for producing variable-surface particles derived from low-temperature melting point eutectic alloys by applying mixing forces and sequential surface reactions. The particles may be multi-layered and include at least one layer of inorganic material and at least one layer of organic material. The particles may be micro- or nano-sized in some embodiments.

The particles described herein may be prepared using a method of shearing molten, or liquid, metals into complex particles. The disclosed approach generally combines both mechanical and chemical principles to create multi-layer micro- and nano-sized particles. The low-temperature melting point metal alloys are effectively broken up into smaller-sized particles under fluid flow with concomitant surface oxidation and functionalization. Further, self-assembly principles may be applied post-synthesis to create unique assembled structures.

The aspects disclosed herein in accordance with the present invention are not limited in their application to the details of construction and the arrangement of components set forth in this description or illustrated in the accompanying drawings. These aspects are capable of assuming other embodiments and of being practiced or of being carried out in various ways. Examples of specific implementations are provided herein for illustrative purposes only and are not intended to be limiting. In particular, acts, components, elements, and features discussed in connection with any one or more embodiments are not intended to be excluded from a similar role in any other embodiments.

Also, the phraseology and terminology used herein is for the purpose of description and should not be regarded as limiting. Any references to examples, embodiments, components, elements or acts herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. In addition, in the event of inconsistent usages of terms between this document and documents incorporated herein by reference, the term usage in the incorporated reference is supplementary to that of this document; for irreconcilable inconsistencies, the term usage in this document controls.

Variable-Surface Particles

In accordance with one or more embodiments, multilayer particles having a variable surface morphology (also referred to as "variable-surface particles") are provided. The particle size may be on a meso, micro, or nanoscale.

The particles may be formed from metal alloys. The alloy may comprise two, three or more metals. The alloy may be a eutectic metal alloy. The eutectic metal alloy may be Field's metal. Field's metal may be an alloy of bismuth, indium, and tin, combined in the following percentages by weight: 32.5% Bi, 51% In, and 16.5% Sn. Field's metal typically melts at approximately 62° C. (144° F.).

In accordance with at least one embodiment, a formed particle comprises an interior core, a surrounding oxide layer, and a surface organic layer. The particle core may be surrounded by at least one layer of inorganic material. As used herein, the term "inorganic material" refers to non-carbon based materials. According to some embodiments, the inorganic material is capable of reacting with metal, including the liquid metals discussed above. Non-limiting examples of inorganic materials include oxides. For example, the at least one layer of inorganic material may be a metal oxide, a metal sub-oxide, or a combination of both. Examples of metal oxides forming the oxide layer, according to certain embodiments, include indium oxide and tin oxide. According to various embodiments, the inorganic material may be produced using any suitable oxidizer with the desired reactivity, non-limiting examples of which include water, oxygen, and hydrogen peroxide.

In accordance with at least one embodiment, the at least one layer of inorganic material is less than 1 nm in thickness. According to some embodiments, the at least one layer of inorganic material is several atoms thick. In certain instances, the at least one layer of oxide may have a thickness of at least about 0.7 nm, and may be made thicker by subjecting the core to further oxidation conditions.

In accordance with some embodiments, at least one layer of organic material is attached to the at least one layer of inorganic material. As used herein, the term "organic material" refers to a carbon-based material. According to certain embodiments, the organic material is capable of attaching to the inorganic material discussed above. In some embodiments, the organic material is a carboxylate species, or derived from a carboxylic acid. For example, carboxylic acids are known to bind to metal oxide surfaces. According to some embodiments, acetic acid binds to the metal oxide to form at least one layer of acetate bound on the oxide. Non-limiting examples of carboxylic acids include saturated aliphatic carboxylic acids having one to 20 carbon atoms such as formic acid, acetic acid, propanoic acid, butyric acid, hexanoic acid, heptanoic acid, octanoic acid, decanoic acid, and higher aliphatic acids such as hexadecanoic acid and octadecanoic acid. The carboxylic acid may be of any length or shape, provided that the carboxylic acid is capable of accessing the surface of the inorganic material. Other examples of carboxylic acids include unsaturated aliphatic carboxylic acids, alicyclic carboxylic acids, aromatic carboxylic acids, and polycarboxylic acids. In accordance with some embodiments, the carboxylic acids may include functional substituents, such as halogen, hydroxyl, nitro, alkyl, alkoxy, aldehyde, ester, and/or cyano groups. For example, one or more additional functional groups may be included in a longer chain acid, including hydrogen bonding groups such as amides. The organic material may be any material that is capable of bonding or otherwise attaching to the inorganic material and contributes toward the functionality of the particle as disclosed herein.

In accordance with at least one embodiment, the particle is a nanoparticle. As used herein, the terms "nano-particle" and "nano-sized particle" are used interchangeably and refer to a particle having a diameter that is less than 100 nanometers (0.1 micron). According to another embodiment, the particle is a micro-particle. As used herein, the terms "micro-particle" and "micro-sized particle" are used interchangeably and refer to a particle having an average diameter of from about 0.1 microns to about 100 microns. Other dimensions are also achievable.

Process

In accordance with one or more embodiments, a method for producing a multilayer metal particle having an irregular surface architecture is provided. According to one embodiment, a molten eutectic metal alloy is introduced into a solution to produce a eutectic-solvent mixture. The eutectic-solvent mixture is sheared for a sufficient period of time to induce surface tension driven phase segregation in the eutectic metal alloy to produce an irregular surface architecture. The eutectic metal alloy is allowed to precipitate out of the mixture to produce a plurality of particles. The particles are then allowed to oxidize in the presence of air. The oxidized particles may be functionalized with an organic species to form an organic layer to produce a multilayer metal particle.

The liquid or molten metal may be provided as discussed and described above, and according to certain aspects, the molten metal remains in molten form when placed into a solution, sometimes referred to as a carrier fluid. The metal alloy may comprise a three metal alloy and may be eutectic alloy, such as Field's metal, as discussed above, with a low melting point (below 200° C.). The solution containing the molten alloy may be referred to as a eutectic-solvent mixture. The solution may comprise various solvents having a boiling point below 250° C. such as water and/or diethylene glycol. The solution may include other components such as the organic species discussed above, including acetic acid or another carboxylic acid. The organic species may serve to functionalize the surface of the particles.

According to some embodiments, the solution serves as a medium for distributing the molten metal alloy. The solution containing the molten alloy may be referred to as a eutectic-solvent mixture. The solution may comprise various solvents having a boiling point below 250° C. such as water and/or diethylene glycol. The solution may include other components such as the organic species discussed above, including acetic acid or another carboxylic acid. The organic species may serve to functionalize the surface of the particles. In accordance with various embodiments, the carrier fluid is a Newtonian fluid, such as water. Newtonian fluids undergo strain rates that are proportional to the applied shear stress, which, according to some aspects, may enhance the predictability of the particle's size and shape. According to alternative embodiments, a non-Newtonian fluid may be used for preparing the particles. The eutectic-solvent mixture may be heated prior to shearing. For example, the mixture may be heated to a temperature in a range from about 95° C. to about 160° C.

In certain embodiments, components in solution with the liquid metal form a layer of inorganic material, as discussed above. For example, according to some embodiments, the at least one carrier fluid is an oxidizer. As used herein, the term "oxidizer" refers to a substance that yields oxygen that is available to bind with the liquid metal. Non-limiting examples of oxidizers include oxygen, air, ozone, hydrogen peroxide, and water. The liquid metal may be oxidized to form an oxide shell. In certain instances the oxide is a thin and self-limiting oxide shell, but as discussed above, the thickness of the oxide layer may be increased by exposing the liquid metal to further oxidizing conditions. For example, heating the liquid metal in the presence of oxygen may increase the thickness of the metal oxide layer.

The organic material may be provided and characterized as previously discussed. According to various aspects, the organic species attaches to the surface of the particle, for example, on the oxide layer, and functionalizes the particles. The organic species may be a carboxylic acid such as acetic acid. Thus, according to certain aspects, the metal oxide shell reacts with the carboxylate species, such as acetate and anchors them.

Figure 4:
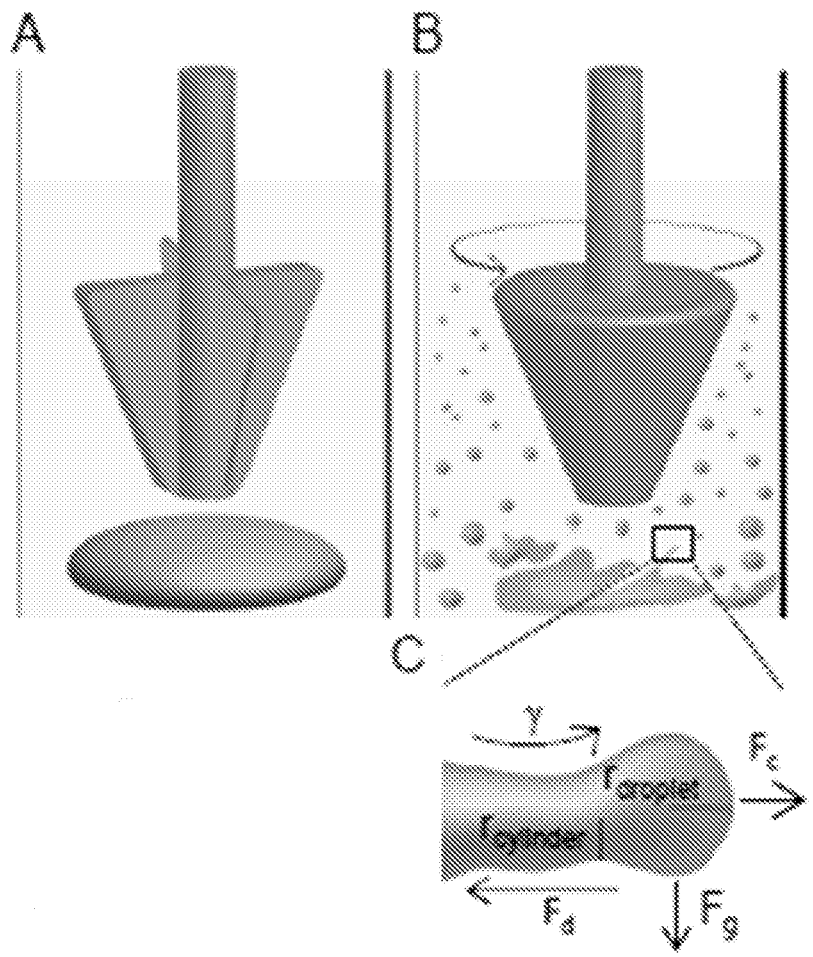
FIG. 4 is a series of schematic illustrations of a method for making variable-surface particles in accordance with one or more aspects of the invention.
Figure 5:
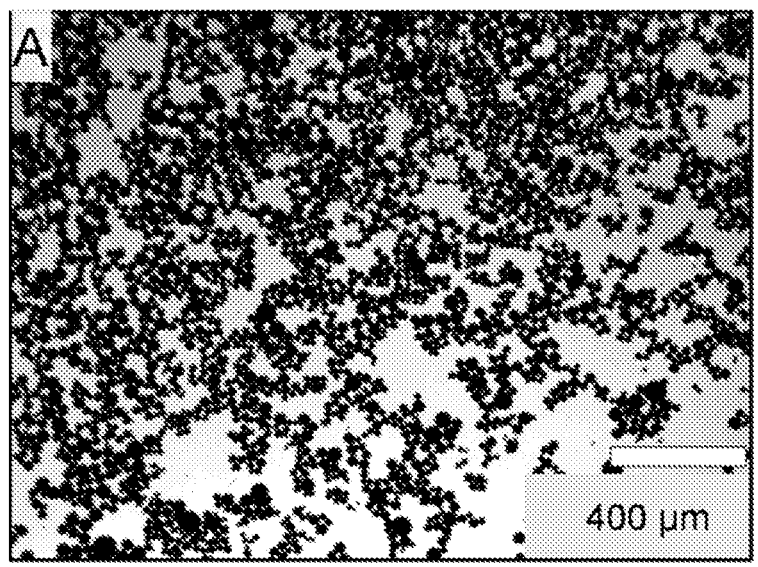
FIG. 5 is a microscope image of a number of microparticles in accordance with one or more aspects of the invention.

According to at least one embodiment, the method further comprises applying mixing forces to the solution to produce a suspension comprising a plurality of particles, as shown in FIGS. 4A and 4B. In accordance with some embodiments, the mixing forces are at least one of shear forces, cavitation forces, milling forces, ultrasonic forces, laser ablation forces, atomization forces, and compressive forces. One or more of these forces may be applied by at least one device, non-limiting examples of which include high pressure homogenizers, jet stream devices, rotar-stator colloid mills, ball mills, high shear mixers, ultrasonic devices, mechanical alloying devices, laser devices, and atomization devices. For example, in accordance with some embodiments, a shearing apparatus may be operated in a turbulent state in order to impart high shearing forces to the liquid metal. Shearing may take place over a period of time in the range of about 5 minutes to about 30 minutes. According to some embodiments, the shear force creates a shear rate in a range of from about 600 s$^{-1}$ to about 3100 s$^{-1}$. For example, according to certain embodiments, the shear force creates a shear rate of about 2300 s$^{-1}$. According to another embodiment, the shear force creates a shear rate of about 3100 s$^{-1}$. As will be appreciated by one of ordinary skill in the art, the mixing forces may be of any magnitude suitable for forming the suspension of particles having desired properties, as disclosed herein. Thus, the shear rate may be greater than 3100 s$^{-1}$, or less than 600 s$^{-1}$, depending on the application and materials used.

In accordance with various aspects, the mixing forces function to break up the liquid metal into smaller droplets. Under this approach, forces acting on a liquid metal droplet include: shear ($\gamma$), gravity ($F_g$), drag ($F_d$), centrifugal forces ($F_c$), and buoyancy ($F_b$, a minor contributor due to density differences), as illustrated in FIG. 4C. For a body immersed in a moving fluid, the nature and intensity of interactions vary with respect to its intrinsic properties and its position around the flowing fluidic body. Initially, at t=0, (i.e. a stationary drop in the presence of a moving fluid, as shown in FIG. 4A), $\gamma$ dominates and stretches the drop into a cylinder-like shape, characterized by period wave-like instabilities, as shown in FIG. 4C. On reaching the Rayleigh-Plateau limit (where the radius $r_{droplet} > 1.5 \ r_{cylinder}$), the cylindrical liquid metal breaks into droplets, as shown in FIG. 4B. Once the droplet is formed, a combination of $F_d$, $F_c$ and $\gamma$ will ultimately split the droplet (i.e., work done on the droplet) until a final limit is attained where no more work is being done on the droplet ($\delta W = 0$). At this mechanical limit, forces acting on the droplet equal the Laplace pressure ($W = \Delta P$) and are directly proportional to the interfacial surface tension, $\gamma_{int}$, between the two liquids and the mean curvature, H, (hence size for spheres) of the droplet, as expressed below in Equation 1.

$$\Delta P = P_{droplet} - P_{fluid} = 2H\gamma_{int} \qquad \text{Equation 1:}$$

where $P_{droplet}$ and $P_{fluid}$ are the pressure in the droplet and the shearing fluid respectively. As the droplet gets smaller, $F_d$ becomes a more dominant force. Drag force, which can be expressed in terms of the drag coefficient $C_d$, is proportional to the relative rate of momentum transported by the fluid, as expressed below in Equation 2.

$$C_d = \frac{2F_d}{A\rho V^2} \qquad \text{Equation 2}$$

where A is the cross-sectional area of the body normal to the velocity vector, V is the velocity of the fluid, and, $\rho$ is the density of the fluid. Since compressible bodies evolve during flow to minimize their surface area (energy), it follows that control of shearing speed and choice of the shearing liquid ($\Delta P \approx W$ limit) can lead to particles of different sizes and/or shapes.

According to some embodiments, the mixing forces are applied for a period of time sufficient to produce a plurality of particles comprising at least one of micro- and nano-sized particles.

According to some embodiments, the shearing force induces a surface tension driven phase segregation within the particle to produce an irregular surface architecture. The Lowengrub-Voigt model on behavior of multicomponent drops under fluidic flow predicts that the surface composition would either evolve to phase-segregate or, at the least, be dynamic giving random compositions. This model predicts that as a drop deforms under shear, the component with smallest surface tension should accumulate on the drop tip where the curvature is largest. When low melting solids are subjected to shearing forces, therefore, any differences in surface composition can be retained upon solidification to give particles with variable surface composition and/or morphologies. Field's metal (Bi 32.5%, In 51%, Sn 16.5%, mp 62° C.), when heated above its melting point, can be subjected to shearing forces to form particles having a variable surface morphology. Applying the Lowengrub-Vogt model to a Field's metal melt, (surface energy of the components; $\gamma_{Sn}$=0.49 J/m2, $\gamma_{In}$≈$\gamma_{Bi}$=0.68 J/m2) suggests that Sn would preferentially phase segregate to the surface when a drop of the melt is subjected to shear stress under fluidic flow. Differences in density ($\rho_{Sn}$=7.27 g/cm3, $\rho_{In}$=7.31 g/cm3, $\rho_{Bi}$=9.79 g/cm3), however, suggest that Bi would precipitate under gravitational and centrifugal forces. When two metals phase segregate out of ternary systems and these metals have different coefficients of linear expansion ($\alpha_{Sn}$=22×10−6 K−1, $\alpha_{Bi}$=13.4×10−6 K−1) and reactivity, the resulting surface is unlikely to be smooth.

In accordance with one or more embodiments, metals oxidize and form a protective oxide layer that may be further stabilized by modification of the oxide surface, such as through acetate. Further, post-synthesis modification allows for the possibility to create the particles, etch them in a non-binding acid, or etch them using a milling technique as discussed below, and then replace the inorganic and/or organic layers with a different inorganic and/or organic layer.

In accordance with some embodiments, the respective concentrations and amounts of the components of the solution may influence one or more aspects of the formed particles, such as their size and shape. According to some embodiments, the solution may include an organic material that is combined with an inorganic material to form a solution of 5-10% organic material present in the inorganic material, such as 5% acetic acid in deionized water, or 10% acetic acid in deionized water. The concentration of organic material and inorganic material may be of any suitable concentration and/or ratio for forming the particles as described herein.

According to some embodiments, the mixing forces and other conditions, such as the ratio of the liquid metal, organic material(s), and other solution components to one another, and other considerations such as the process duration, temperature, and pressure, may each be adjusted to produce particles of different sizes and shapes. According to some embodiments, process temperature may affect the average size of the resulting particles. In accordance with some aspects, increasing the pressure may also increase the rate of the reactions, such as the oxidation reaction discussed above between the liquid metal and oxidizer. According to another example, when less carrier fluid is present, then the density of the liquid metal particles in the suspension increases, and as a consequence, the average diameter of the particles also increases. According to yet another example, when the amount of organic material present in the solution increases, such as the carboxylic acid, then the speed of dissolution of the metal particles by the acid also increases, and subsequently the diameter of the particles also increases.

In accordance with a further aspect, the intensity of the mixing force also has an effect on the size of the resulting particles. For example, the type and/or speed of a shearing device may cause a corresponding increase or decrease in particle size. According to one example, a shearing device with a speed of 17,700 rpm and a rotor assembly having a diameter of 42 mm creates higher shear forces and thus smaller particles than a shearing device with a slower speed of 11,600 rpm and a 13 mm diameter rotor assembly.

In accordance with some embodiments, the method further comprises removing at least a portion of the plurality of particles from the suspension. For example, particles may be separated from the suspension using any one of a number of devices and techniques known to those of ordinary skill in the art. Non-limiting examples of removal methods include settling, filtration, and centrifugation. The particles may then be further processed, depending on the desired application.

According to at least one aspect, and as discussed above, the particles may undergo further surface modification post-synthesis. For example, the carboxylic acid group may function as an anchoring group, and any application-specific group may be attached on the other end of this organic molecule. For instance, a specific peptide sequence that may be used to bind to cells may be attached. In addition, functional groups may be attached that function to directly assemble the particle. According to certain embodiments, a multi-dentate ligand allows for this type of flexible functionality. This type of structure allows for a molecule with multiple binding functional groups to use one functional group to bind to the metal oxide, and leave others available for attachment and/or provide other functionalities.

In accordance with one or more embodiments, two or more particles may be fused to form different shapes through capillary-driven self-assembly mechanisms. For instance, two or more particles of different shapes and sizes may be combined to form an asymmetric assembly. According to certain aspects, the particles may be self-assembled into chains via capillary self-assembly. Drying the particles may induce the formation of self-assembled aggregated particles. Without being bound by theory, it is believed that as suspensions of the droplets dry, water pulls the particles together though capillary forces, which is strong enough to deform the particles where they touch one another to form flat regions.

Without being bound by theory, it is believed that the assemblies of particles are formed from either grouping smaller particles together, or are triggered by a larger particle formed from the coalescence of smaller particles.

Figure 11:
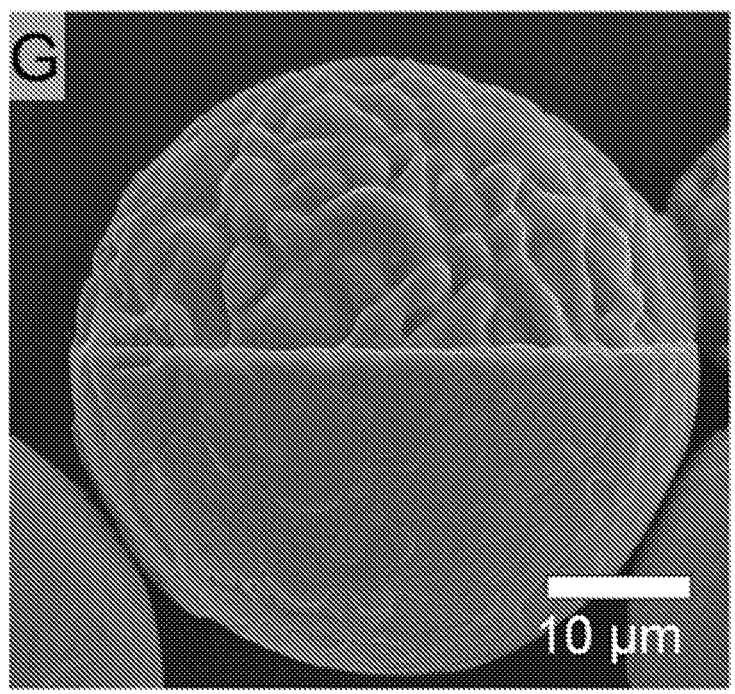
FIG. 11 is an SEM image of a partially milled variable-surface particle in accordance with one or more aspects of the invention.

In some embodiments, the particles may be modified by etching one or more of the inorganic and organic layers. According to certain aspects, this technique may be used to create new particles with different physical properties. In accordance with one embodiment, a focused ion beam (FIB) of gallium ions may be used to gently mill away a section of the outer surface of a particle. Using this technique, a metal ion may be accelerated in an electric field toward the particle and the resulting kinetic energy gently removes the exposed surface. For example, FIG. 11 illustrates a partially-milled particle. As shown in FIG. 11, the initial surface of the particle has a smooth texture and as the particles are milled, a rougher surface is exposed.

EXAMPLE

The functions and advantages of the embodiments discussed above will be more fully understood from the example outlined below. The following example is intended to be illustrative in nature, and is not intended to limit the scope of the disclosure.

A 10 mL aliquot of 5% (v/v) acetic acid in deionized water or diethylene glycol was placed into a 4 dram screw-top glass vial with a 28 mm outer diameter and 57 mm height. 1.1 g of molten bismuth indium tin was directly added to the solution. The experiment was heated in an oil bath to 95 or 160° C. The metal was melted at these temperatures. The liquid bismuth indium tin metal was sheared using a PTFE shearing implement. The PTFE shearing implement was rotated at 11,600 rpm. Shearing time was varied from 5 to 20 min. The experiment was removed from the hot oil bath, and PTFE shearing implement was slowed to a stop over 1 minute. The solution was cooled to room temperature while stiffing. The resulting suspension was allowed to sediment for 5 to 10 min, and the resulting precipitate was collected, diluted in ethanol 8×, drop-cast on silicon, dried, and analyzed by scanning electron microscopy.

Figure 6:
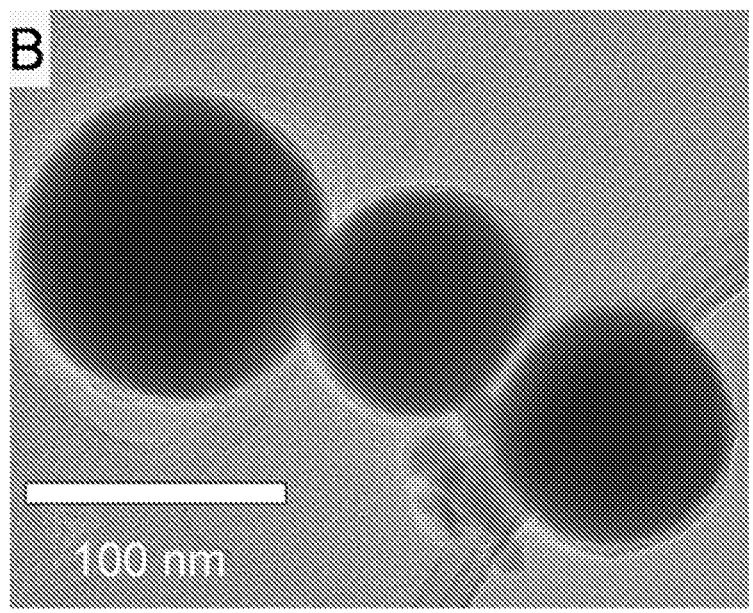
FIG. 6 is a transmission electron microscope (TEM) image in accordance with one or more aspects of the invention.
Figure 7:
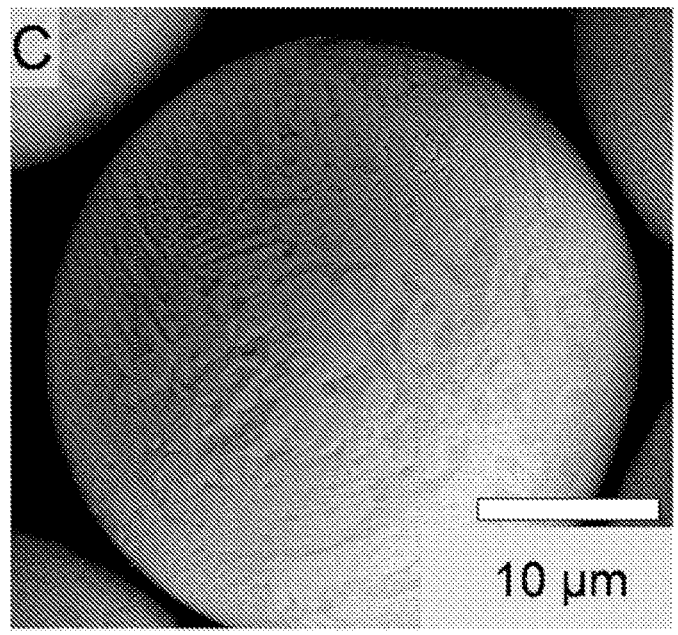
FIGS. 7-10 present SEM images of variable-surface particles in accordance with one or more aspects of the invention.
Figure 8:
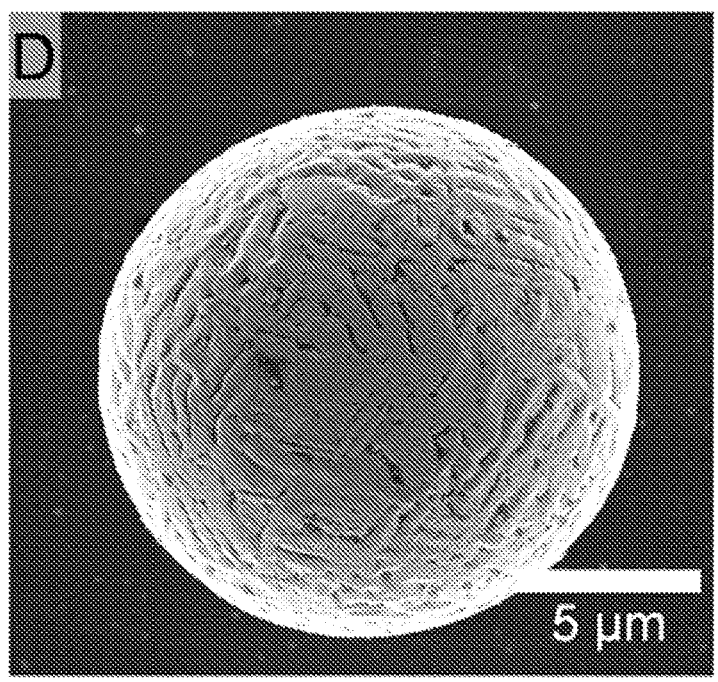

The yield was a 170 µg/mL suspension of fine particles. Resulting particles are shown in FIGS. 5-11. These fine suspensions slowly settled over time. Large quantities of micro-particles were observed under a light microscope (FIG. 5) and homogeneous looking nano-particles were observed by TEM (FIG. 6). Average particle sizes measured by SEM were 12.6±8.9 µm.

Figure 9:
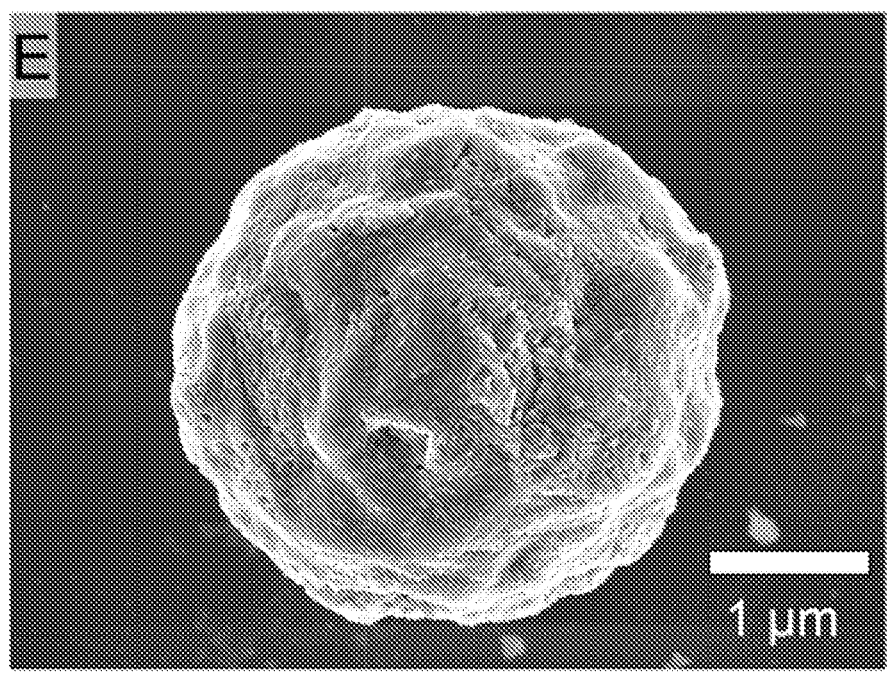
Figure 10:
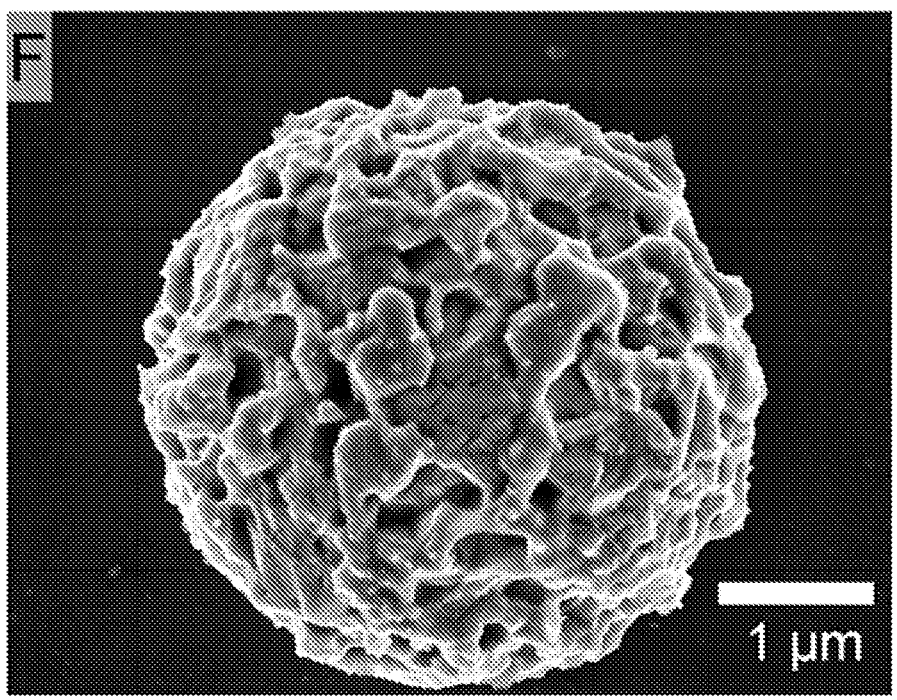

Two phase segregated domains on the surface of the particles were observed, as shown in FIG. 9. Belts of a smooth top layer partially cover the surface of the particle, while below it a rougher layer is observed. Elemental mapping revealed the two phase segregated regions as bismuth and tin rich with indium being evenly distributed throughout the particles. These results suggest that density and surface tension, as predicted, are important variables in creating particles of varied surface compositions using the disclosed methods. The presence of tin, instead of only the heavier bismuth, on the outer surface of the particles supports the Lowengrub-Vogt model and further demonstrates the applicability of fluid dynamics in creating complex structures.

The phase-segregated particles showed various surface morphologies by SEM. Round particles were observed with the following: lamellar type texture (FIG. 7) (formed by shearing in a 5% acetic acid solution in diethylene glycol at 11 600 rpm for 20 min), smooth woven texture, "surface rods" (FIG. 8), bumpy surfaces (FIG. 9), rough porous surfaces (FIG. 10), and patches of alternating swirls of smooth and rough textures.

Internal phase separation was probed by partially milling half of a particle (FIG. 11) followed by elemental mapping of the whole particle and imaging using energy selective backscattered (EsB) detector. Phase separated tin was observed in the core of these particles but in smaller patches and in patterns that do not mirror the enrichment observed on the surface. The striation (FIG. 7), porosity (FIG. 8), or the lamellar type (FIG. 9) patterns were not observed in the core of the particles, but as expected, random enrichment of one metal over the others was observed indicating that the patterns observed on the surface of the particles are due to a surface phenomenon. These results confirm that the disclosed methods can be used to engineer surface composition, an important parameter in applications such as catalysis.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A method of making a multilayer metal particle having an irregular surface architecture, the method comprising:
    introducing a molten eutectic metal alloy into a solution to produce a eutectic-solvent mixture;
    shearing the eutectic-solvent mixture for a sufficient period of time to induce surface tension driven phase segregation in the molten eutectic metal alloy to produce an irregular surface architecture on the eutectic metal alloy;
    allowing the molten eutectic metal alloy to precipitate to produce a plurality of particles;
    allowing the plurality of particles to oxidize in the presence of an oxidizer; and
    functionalizing the particles with an organic species to form an organic layer to produce a multilayer metal particle having an irregular surface architecture.

2. The method of claim 1, wherein the period of time for shearing is in the range of about 5 minutes to about 30 minutes.

3. The method of claim 1, wherein functionalizing the particles comprises functionalizing the particles with a carboxylate species.

4. The method of claim 3, wherein the carboxylate species comprises acetate.

5. The method of claim 4, wherein the solution comprises acetic acid.

6. The method of claim 5, wherein the solution comprises acetic acid and a solvent having a boiling point below 250° C. to produce a 5% acetic acid solution.

7. The method of claim 6, wherein the solvent comprises one of water or diethylene glycol.

8. The method of claim 1, wherein the molten eutectic metal alloy is a three-component alloy with a melting point below 200° C.

9. The method of claim 8, wherein the molten eutectic metal alloy comprises Field's metal having 32.5% bismuth, 51% indium, and 16.5% tin by weight.

10. The method of claim 1, further comprising drying the particles to induce the formation of self-assembled aggregated particles.

11. The method of claim 1, further comprising heating the eutectic-solvent mixture before shearing.

12. The method of claim 11, further comprising heating the eutectic-solvent mixture to a temperature in a range of from about 95° C. to about 160° C.

13. The method of claim 12, further comprising cooling the mixture to room temperature during the shearing step.

14. The method of claim 1, further comprising milling the multilayer particle into a desired shape.

15. The method of claim 14, wherein milling comprises subjecting the multilayer particle to a focused ion beam.

16. A multilayer nano- or micro-particle comprising at least three metals and having an irregular surface architecture.

17. The multilayer particle of claim 16, wherein the multilayer particle comprises an interior core, a surrounding oxide layer, and a surface organic layer.

18. The multilayer particle of claim 17, wherein the irregular surface architecture comprises at least one of the following: a lamellar texture, a smooth woven texture, a rough solid texture, a rough porous surface, and a porous texture.

19. The multilayer particle of claim 17, wherein the multilayer particle comprises bismuth, indium, and tin.

20. The multilayer particle of claim 19, wherein the multilayer particle comprises Field's metal.

21. The multilayer particle of claim 20, wherein the oxide layer comprises at least one of indium oxide and tin oxide.

22. The multilayer particle of claim 17, wherein the surface organic layer comprises acetate or a carboxylate species.

23. The multilayer particle of claim 22, wherein the carboxylate species comprises acetate.

24. The multilayer particle of claim 17, wherein the oxide layer has a thickness of at least about 0.7 nm.

25. A pharmaceutical agent or a catalyst comprising the multilayer particle of claim 16.

* * * * *

UNITED STATES PATENT AND TRADEMARK OFFICE
CERTIFICATE OF CORRECTION

PATENT NO. : 10,124,310 B2
APPLICATION NO. : 15/521518
DATED : November 13, 2018
INVENTOR(S) : Martin Thuo et al.

Page 1 of 1

It is certified that error appears in the above-identified patent and that said Letters Patent is hereby corrected as shown below:

In the Specification

Column 3, Line 44, delete "stiffing" and insert -- stirring --.
Column 10, Line 66, delete "stiffing" and insert -- stirring --.

Signed and Sealed this
Twenty-fifth Day of December, 2018

Andrei Iancu
*Director of the United States Patent and Trademark Office*